United States Patent
Kudoh et al.

(10) Patent No.: US 12,006,524 B2
(45) Date of Patent: Jun. 11, 2024

(54) METHOD FOR PRODUCING UROLITHINS

(71) Applicant: DAICEL CORPORATION, Osaka (JP)

(72) Inventors: Masatake Kudoh, Myoko (JP); Takanori Nakajima, Myoko (JP); Hiroaki Yamamoto, Myoko (JP)

(73) Assignee: DAICEL CORPORATION, Osaka (JP)

( * ) Notice: Subject to any disclaimer, the term of this patent is extended or adjusted under 35 U.S.C. 154(b) by 1240 days.

(21) Appl. No.: 16/473,385

(22) PCT Filed: Dec. 26, 2017

(86) PCT No.: PCT/JP2017/046787
§ 371 (c)(1),
(2) Date: Jun. 25, 2019

(87) PCT Pub. No.: WO2018/124135
PCT Pub. Date: Jul. 5, 2018

(65) Prior Publication Data
US 2019/0323045 A1    Oct. 24, 2019

(30) Foreign Application Priority Data

Dec. 26, 2016 (JP) .................................. 2016-251761
Apr. 10, 2017 (JP) .................................. 2017-077536

(51) Int. Cl.
| | |
|---|---|
| *C12P 17/06* | (2006.01) |
| *A23L 33/105* | (2016.01) |
| *C12N 1/20* | (2006.01) |
| *C12R 1/145* | (2006.01) |

(52) U.S. Cl.
CPC ............ *C12P 17/06* (2013.01); *A23L 33/105* (2016.08); *C12N 1/205* (2021.05); *A23V 2002/00* (2013.01); *C12R 2001/145* (2021.05)

(58) Field of Classification Search
CPC .......... C12P 17/06; C12P 7/22; A23L 33/105; C12N 1/205; C12R 2001/145
See application file for complete search history.

(56) References Cited

FOREIGN PATENT DOCUMENTS

| CN | 101375846 B | * | 7/2013 | .......... A61K 31/366 |
| WO | WO 2014/0147280 A1 | | 9/2014 | |

OTHER PUBLICATIONS

Extended European Search Report for European Application No. 17889029.9, dated Sep. 2, 2020.
García-Villalba et al., "Time Course Production of Urolithins from Ellagic Acid by Human Gut Microbiota," J. Agric. Food Chem, vol. 61, 2013, pp. 8797-8806 (10 pages).
Gímenez-Bastida et al., "Intestinal Ellagitannin Metabolites Ameliorate Cytokine-Induced Inflammation and Associated Molecular Markers in Human Colon Fibroblasts", J. Agric. Food Chem, vol. 60, 2012, 8866-8876 (11 pages).
International Preliminary Report on Patentability and Written Opinion of the International Searching Authority dated Jul. 11, 2019, for International Application No. PCT/JP2017/046787.
International Search Report, dated Apr. 3, 2018, for International Application No. PCT/JP2017/046787.
Ishimoto et al., "Antioxidative Properties of Functional Polyphenols and Their Metabolites Assessed by an ORAC Assay", Biosci. Biotechnol. Biochem, vol. 76, No. 2, 2012, pp. 395-399 (5 pages).
Ito et al., "Identification of Urinary and Intestinal Bacterial Metabolites of Ellagitannin Geraniin in Rats," J. Agric. Food Chem., vol. 56, 2008, pp. 393-400 ( 8 pages).
Mohan et al., "Clostridium asparagiforme sp. nov., isolated from a human faecal sample", Systematic and Applied Microbiology, vol. 29, 2006, pp. 292-299 (8 pages).
Nuñez-Sánchez et al., "Targeted metabolic profiling of pomegranate polyphenols and urolithins in plasma, urine and colon tissues from colorectal cancer patients," Mol. Nutr. Food Res., vol. 58, 2014, pp. 1199-1211 (13 pages).
Ryu et al., "Urolithin A induces mitophagy and prolongs lifespan in C. elegans and increases muscle function in rodents," Nature Medicine, 2016 (published online Jul. 11, 2016), 14 pages.
Selma et al., "Description of urolithin production capacity from ellagic acid of two human intestinal Gordonibacter species," Food & Function Accepted Manuscript, vol. 5, No. 8, 2014, pp. 1-21 (22 pages).
Verzelloni et al., "Antiglycative and neuroprotective activity of colon-derived polyphenol catabolites," Mol. Nutri. Food Res., vol. 55, 2011, pp. S35-S43 (9 pages).
Warren et al., "Clostridum aldenense sp. nov. and Clostridium citroniae sp. nov. Isolated from Human Clinical Infections," Journal of Clinical Microbiology, vol. 44, No. 7, Jul. 2006, pp. 2416-2422 (7 pages).

* cited by examiner

*Primary Examiner* — Lynn Y Fan
(74) *Attorney, Agent, or Firm* — Birch, Stewart, Kolasch & Birch, LLP

(57) ABSTRACT

An object of the present invention is to provide a method for eliminating the hydroxyl group at the 9-position of a urolithin to produce another kind of urolithin. This object is achieved by a method for producing a second urolithin, including Step (a): allowing, in a solution containing a first urolithin, a microorganism having an ability to produce the second urolithin from the first urolithin to produce the second urolithin from the first urolithin.

18 Claims, No Drawings

METHOD FOR PRODUCING UROLITHINS

TECHNICAL FIELD

The present invention relates to a method for producing urolithins.

BACKGROUND ART

Urolithins, represented by urolithin A and urolithin C, are known to be metabolites of ellagic acid derived from, for example, ellagitannin contained in pomegranate, raspberry, blackberry, cloudberry, strawberry, walnut, and the like.

Ellagitannin is classified as a hydrolyzable tannin, and known to be hydrolyzed in the body after ingestion, to be converted into ellagic acid. Ellagic acid per se is also present in fruits and the like.

Regarding production of urolithins in the body, production of urolithins from ellagitannin such as geraniin in rat has been shown by analysis of urinary urolithins (Non-patent Document 1).

It has also been reported that, in human, urinary urolithins were detected following ingestion of a pomegranate extract containing ellagitannin composed mainly of punicalagin, and that urolithin A and urolithin C are major ellagic acid metabolites (Non-patent Document 2).

These urolithins are known to have a variety of physiological activities, and expected to be useful as materials of drugs, cosmetics, and foods and drinks.

For example, urolithin A has been reported to have functions such as antioxidant action (Non-patent Document 3), anti-inflammatory action (Non-patent Document 4), anti-saccharification action (Non-patent Document 5), and mitophagy-promoting action (Non-patent Document 6), and therefore its development as a material having anti-aging function has been expected.

As an example of methods for synthesizing these urolithins, a method in which 2-bromo-5-methoxybenzoic acid as a starting material is demethylated to produce 2-bromo-5-hydroxybenzoic acid, and then reaction with resorcinol is performed to obtain urolithin A, has been reported (Non-patent Document 1). However, such a chemical synthesis method is not suitable for use of urolithins as materials of functional foods (including drinks and supplements).

It is known that ellagitannin and ellagic acid, after ingestion into the body, undergo metabolism by the intestinal microbial flora to be converted to urolithins. Recently, a microorganism belonging to *Gordonibacter urolithinfaciens* was isolated and identified as an intestinal bacterium that produces urolithin C, which is a urolithin, from ellagic acid, and a method for producing urolithin C by fermentation of ellagic acid using this intestinal bacterium has been reported (Patent Document 1, Non-patent Document 7). However, the accumulated concentration of urolithin C in the fermentation liquid was only about 2 mg/L, and urolithin A, which is a major ellagic acid metabolite in human, cannot be produced.

A microorganism belonging to *Gordonibacter pamelaeae*, which belongs to the genus *Gordonibacter*, has also been reported to produce urolithin C from ellagic acid. However, production of urolithin A has not been reported. No microorganism, including this microorganism, has been reported to be capable of eliminating the hydroxyl group at the 9-position of a urolithin to produce another kind of urolithin.

PRIOR ART DOCUMENTS

Patent Document

[Patent Document 1] WO 2014/147280

Non-Patent Documents

[Non-patent Document 1] J. Agric. Food Chem. 56, 393-400 (2008)
[Non-patent Document 2] Mol. Nutr. Food Res. 58, 1199-1211 (2014)
[Non-patent Document 3] Biosci. Biotechnol. Biochem. 76, 395-399 (2012)
[Non-patent Document 4] J. Agric. Food Chem. 60, 8866-8876 (2012)
[Non-patent Document 5] Mol. Nutr. Food Res. 55, S35-S43 (2011)
[Non-patent Document 6] Nature Medicine, 22, 879-888 (2016)
[Non-patent Document 7] Food Func., 5, 8, 1779-1784 (2014)

SUMMARY OF THE INVENTION

Problems to be Solved by the Invention

An object of the present invention is to provide a method of eliminating the hydroxyl group at the 9-position of a urolithin to produce another kind of urolithin.

Means for Solving the Problems

In order to solve the problem described above, the present inventors intensively studied to discover a microorganism having an ability to eliminate the hydroxyl group at the 9-position of a urolithin to produce another kind of urolithin, thereby completing the present invention. The present invention is as follows.

[1] A method for producing a second urolithin represented by the following General Formula (2), comprising the following Step (a):

Step (a): allowing, in a solution containing a first urolithin represented by the following General Formula (1), a microorganism having an ability to produce the second urolithin represented by the following General Formula (2) from the first urolithin to produce the second urolithin from the first urolithin

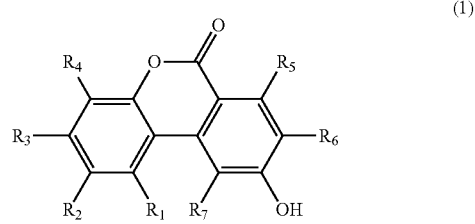

(wherein $R_1$ to $R_7$ each represent a hydroxyl group, a hydrogen atom, or a methoxy group, and at least one of $R_1$ to $R_7$ represents a hydroxy group)

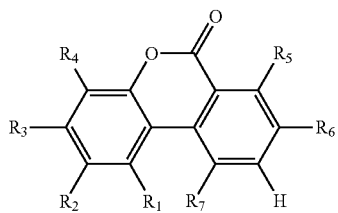

(2)

(wherein $R_1$ to $R_7$ are identical to the $R_1$ to $R_7$, respectively, of the first urolithin represented by the General Formula (1)).

[2] The production method according to [1], wherein the combination of the first urolithin and the second urolithin is a combination of urolithin M5 and urolithin E, respectively, a combination of urolithin M6 and urolithin M7, respectively, a combination of urolithin C and urolithin A, respectively, or a combination of isourolithin A and urolithin B, respectively.

[3] The production method according to [1] or [2], wherein the microorganism is a microorganism belonging to the genus *Clostridium*.

[4] The production method according to [3], wherein the microorganism belonging to the genus *Clostridium* is at least one selected from the group consisting of a microorganism belonging to *Clostridium bolteae*, a microorganism belonging to *Clostridium asparagiforme*, and a microorganism belonging to *Clostridium citroniae*.

[5] The production method according to [4], wherein the microorganism belonging to *Clostridium bolteae* is at least one selected from the group consisting of the *Clostridium bolteae* JCM 12243 strain, DSM 15670 strain, and DSM 29485 strain.

[6] The production method according to [4] or [5], wherein the microorganism belonging to *Clostridium asparagiforme* is the *Clostridium asparagiforme* DSM 15981 strain.

[7] The production method according to any one of [4] to [6], wherein the microorganism belonging to *Clostridium citroniae* is the *Clostridium citroniae* DSM 19261 strain.

[8] The production method according to any one of [2] to [7], wherein the combination of the first urolithin and the second urolithin is a combination of urolithin C and urolithin A, respectively.

[9] The production method according to [8], wherein the urolithin C is obtained by allowing, in a solution containing a raw material of urolithin C, a microorganism having an ability to produce urolithin C from the raw material of urolithin C to produce urolithin C from the raw material of urolithin C.

[10] The production method according to [8], further comprising the following Step (b1):

Step (b1): allowing, in a solution containing a raw material of urolithin C, a microorganism having an ability to produce urolithin C from the raw material of urolithin C to produce urolithin C from the raw material of urolithin C; wherein the Step (a) and the Step (b1) are carried out in the same system.

[11] The production method according to [9] or [10], wherein the microorganism having an ability to produce urolithin C from the raw material of urolithin C is a microorganism belonging to the genus *Gordonibacter*.

[12] The production method according to [11], wherein the microorganism belonging to the genus *Gordonibacter* is a microorganism belonging to *Gordonibacter pamelaeae* and/or a microorganism belonging to *Gordonibacter urolithinfaciens*.

[13] The production method according to [12], wherein the microorganism belonging to *Gordonibacter pamelaeae* is the *Gordonibacter pamelaeae* DSM 19378 strain.

[14] The production method according to [12] or [13], wherein the microorganism belonging to *Gordonibacter urolithinfaciens* is the *Gordonibacter urolithinfaciens* DSM 27213 strain.

[15] The production method according to any one of [9] to [14], wherein the raw material of urolithin C is ellagic acid and/or ellagitannin.

[16] The production method according to any one of [1] to [15], wherein the Step (a) is carried out in an environment with a gas phase containing hydrogen.

[17] The production method according to [16], wherein the ratio of the hydrogen in the gas phase is not less than 0.5% and not more than 20%.

[18] The production method according to any one of [8] to [17], wherein, in the Step (a), the solution containing urolithin C further contains at least one selected from the group consisting of inclusion compounds of α-cyclodextrin, β-cyclodextrin, and γ-cyclodextrin.

[19] The production method according to [18], wherein the total amount of the inclusion compound in terms of the molar ratio to the urolithin C is not less than 0.1 equivalents and not more than 5.0 equivalents.

[20] The production method according to any one of [10] to [19], wherein, in the Step (b1), the solution containing the raw material of urolithin C further contains at least one selected from the group consisting of inclusion compounds of α-cyclodextrin, β-cyclodextrin, and γ-cyclodextrin.

[21] The production method according to [20], wherein the total amount of the inclusion compound in terms of the molar ratio to the total amount of the ellagic acid and/or the ellagitannin is not less than 0.2 equivalents and not more than 10.0 equivalents.

[22] A method for producing a food or drink containing urolithin A, comprising the following Steps (a1) and (c):

Step (a1): allowing, in a solution containing urolithin C, a microorganism having an ability to produce urolithin A from urolithin C to produce urolithin A from urolithin C; and Step (c): mixing the urolithin A produced in the Step (a1) with a raw material of the food or drink to prepare the food or drink.

Effect of the Invention

According to the present invention, a method for eliminating, from a urolithin having a hydroxyl group at the 9-position, the hydroxyl group at the 9-position to produce another kind of urolithin can be provided. By using urolithins obtained by the production method of the present invention for cosmetics, quasi drugs, medical products, sanitary articles, drugs, foods and drinks (including supplements), and the like, production of effects such as antioxidant action, anti-inflammatory action, anti-saccharification action, mitophagy-promoting action, and the like can be expected.

MODE FOR CARRYING OUT THE INVENTION

In the present description, the accession numbers of microbial strains beginning with the letters "DSM" are numbers given to microorganisms stored in DSMZ (Deutsche Sammlung von Mikroorganismen and Zellkulturen GmbH). The accession numbers of microbial strains beginning with the letters "JCM" are numbers given to microorganisms stored in the RIKEN Bioresource Center.

The present invention includes a method for producing a urolithin (first invention) and a method for producing a food or drink containing a urolithin (second invention).

Table 1 shows specific examples of urolithins.

TABLE 1

Table 1. Types of Urolithins

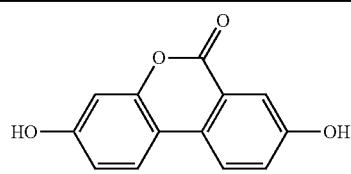
Urolithin A

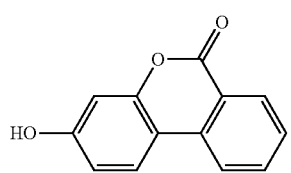 [SMILES: O=c1oc2cc(O)ccc2c2ccccc12]
Urolithin B

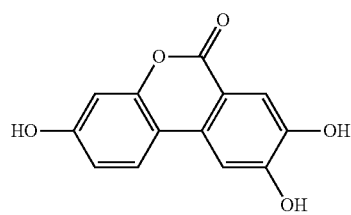 [SMILES: O=c1oc2cc(O)ccc2c2cc(O)c(O)cc12]
Urolithin C

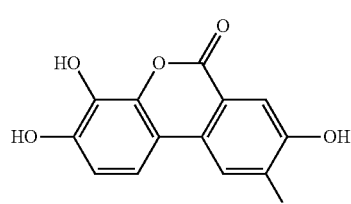
Urolithin D

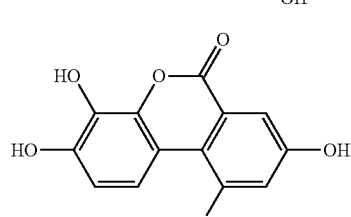
Urolithin E

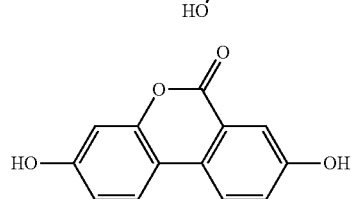
Urolithin M3

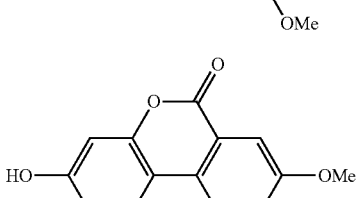
Urolithin M4

TABLE 1-continued

Table 1. Types of Urolithins

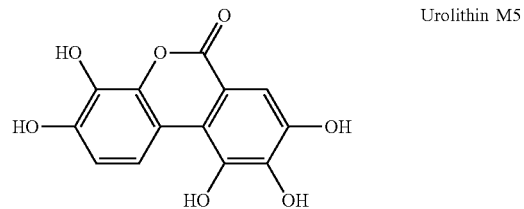
Urolithin M5

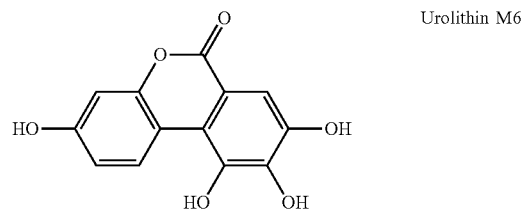
Urolithin M6

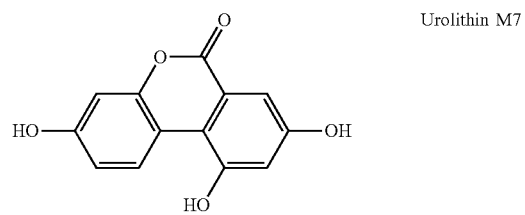
Urolithin M7

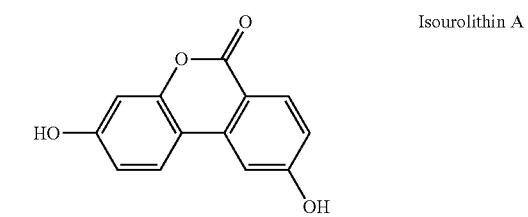
Isourolithin A

<1. Method for Producing Urolithin>

The method for producing a urolithin as the first invention of the present invention includes the following Step (a), and the method may also include other steps.

(1) Step (a)

Step (a) is a step of allowing, in a solution containing a first urolithin represented by the following General Formula (1), a microorganism having an ability to produce a second urolithin represented by the following General Formula (2) from the first urolithin to produce the second urolithin from the first urolithin

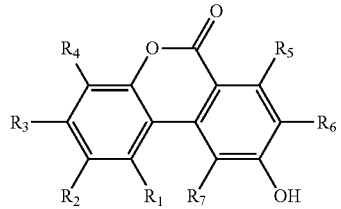

(1)

(wherein $R_1$ to $R_7$ each represent a hydroxyl group, a hydrogen atom, or a methoxy group, and at least one of $R_1$ to $R_7$ represents a hydroxy group)

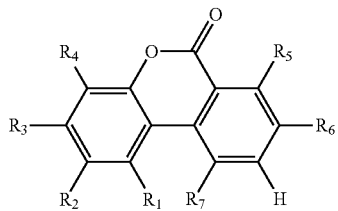

(2)

(wherein $R_1$ to $R_7$ are identical to the $R_1$ to $R_7$, respectively, of the first urolithin represented by the General Formula (1)).

Specific examples of the first urolithin include urolithin C, urolithin D, urolithin M4, urolithin M5, urolithin M6, and isourolithin A.

The second urolithin is the same as the first urolithin except that the hydroxyl group at the 9-position of the first urolithin is eliminated.

The first urolithin in the present invention is preferably urolithin M5, urolithin M6, urolithin C, or isourolithin A. In these cases, the second urolithin in the present invention is urolithin E, urolithin M7, urolithin A, or urolithin B, respectively.

(Microorganism Having Ability to Produce Second Urolithin from First Urolithin)

The microorganism having an ability to produce the second urolithin from the first urolithin in the first invention of the present invention is not limited as long as it is a microorganism having an ability to produce the second urolithin from the first urolithin. The microorganism is preferably an anaerobic microorganism.

Specific examples of the microorganism include microorganisms belonging to the genus *Clostridium*. More specifically, examples of the microorganism include microorganisms belonging to *Clostridium bolteae*, microorganisms belonging to *Clostridium asparagiforme*, and microorganisms belonging to *Clostridium citroniae*.

Examples of the microorganisms belonging to *Clostridium bolteae* include the DSM 29485 strain, DSM 15670 strain, and JCM 12243 strain.

Examples of the microorganisms belonging to *Clostridium asparagiforme* include the DSM 15981 strain.

Examples of the microorganisms belonging to *Clostridium citroniae* include the DSM 19261 strain.

One or more of the above microorganisms may be used irrespective of the genus, the species, and the strain of each microorganism.

The microorganism having an ability to produce the second urolithin from the first urolithin in the first invention of the present invention is not limited to the same microbial strain as each deposited microbial strain described above, and may be substantially the same microbial strain as each of the DSM 29485 strain, DSM 15670 strain, JCM 12243 strain, DSM 15981 strain, and DSM 19261 strain. The substantially the same microbial strain means a microorganism whose base sequence of the 16S rRNA gene has a homology of not less than 97.5%, preferably not less than 98%, more preferably 99%, to the base sequence of the 16S rRNA gene of each microbial strain described above. As long as the effect of the present invention is not deteriorated, the microorganism having an ability to produce the second urolithin from the first urolithin may be a microbial strain prepared by mutagenesis, genetic recombination, selection of a natural mutant strain, or the like from any of the microbial strains, or from a microbial strain which is substantially the same as any of the microbial strains. This applies to all microorganisms described in the present description.

(Resting Cells of Microorganism Having Ability to Produce Second Urolithin from First Urolithin)

The microorganism having an ability to produce the second urolithin from the first urolithin in the first invention of the present invention also includes resting cells thereof. The "resting cells" means cells prepared by removing medium components by an operation such as centrifugation from a cultured microorganism, and washing the resulting cells with water, a salt solution such as physiological saline, or a buffer, followed by suspending the cells in the same liquid as the washing liquid, wherein the cells prepared are in a non-growing state. In the first invention of the present invention, the "resting cells" means cells at least having a metabolic system capable of producing the second urolithin from the first urolithin. The buffer is preferably phosphate buffer, Tris-HCl buffer, citrate-phosphate buffer, citrate buffer, MOPS buffer, acetate buffer, glycine buffer, or the like. The pH and the concentration of the buffer may be adjusted appropriately according to a conventional method.

All microorganisms described in the present description include their resting cells, and the same definition as described above applies thereto.

(Solution Containing First Urolithin)

The solution containing the first urolithin in the first invention of the present invention is not limited as long as the microorganism having the ability to produce the second urolithin from the first urolithin can be allowed to produce the second urolithin from the first urolithin in the solution. The solution is preferably a medium, more preferably a medium described in the later-described "Medium, and Production of Second Urolithin by Culture" section. In cases where the microorganism having the ability to produce the second urolithin from the first urolithin is resting cells, the above-described salt solution or buffer is preferred.

The "medium" as described in the present description means a solution containing a minimum medium and capable of allowing growth of the microorganism. The medium thus does not include a solution such as the above-described salt solution or buffer, which does not allow growth of the microorganism.

In cases where the first urolithin is added to the solution, it may be added either before or during the production of the second urolithin, and may be added at once, sequentially, or continuously.

The content of the first urolithin in the solution is usually not less than 0.01 g/L, preferably not less than 0.1 g/L, more preferably not less than 1 g/L. On the other hand, the content is usually not more than 100 g/L, preferably not more than 20 g/L, more preferably not more than 10 g/L.

(Medium, and Production of Second Urolithin by Culture)

In Step (a), the solution is preferably a medium. The medium is not limited, and examples of the medium include ANAEROBE BASAL BROTH (ABB medium), manufactured by Oxoid Limited; Wilkins-Chalgren Anaerobe Broth (CM0643), manufactured by Oxoid Limited; and GAM medium and modified GAM medium, manufactured by Nissui Pharmaceutical Co., Ltd.

These media are preferably supplemented with an inducer that induces an enzyme that produces the second urolithin from the first urolithin. Examples of the inducer include urolithins other than the first urolithin and the second urolithin, and precursors thereof; ellagic acid; and ellagitannin, which is a precursor of ellagic acid. One or more of the inducers may be used.

A water-soluble organic matter may also be added to the medium as a carbon source. Examples of the water-soluble organic matter include the following compounds: sugars such as glucose, arabinose, sorbitol, fructose, mannose, sucrose, trehalose, and xylose; alcohols such as glycerol; and organic acids such as valeric acid, butyric acid, propionic acid, acetic acid, formic acid, and fumaric acid.

The concentration of the organic matter added to the medium as a carbon source may be appropriately adjusted such that efficient growth is possible. In general, the amount of the organic matter added may be selected within the range of 0.1 to 10 wt/vol %.

In addition to the carbon source, a nitrogen source may be added to the medium. As the nitrogen source, various nitrogen compounds applicable to ordinary fermentation may be used.

Examples of preferred inorganic nitrogen sources include ammonium salts and nitrates, more preferably ammonium sulfate, ammonium chloride, ammonium phosphate, ammonium hydrogen phosphate, potassium nitrate, and sodium nitrate.

Examples of organic nitrogen sources include amino acids, yeast extracts, peptones (for example, polypeptone N), meat extracts (for example, Ehrlich bonito extract, Lab-Lemco powder, and bouillons), liver extracts, and digested serum powders.

In addition of the carbon source and the nitrogen source, inorganic compounds, for example, cofactors such as vitamins, and various salts, may be added to the medium to enhance the growth and the activity in some cases. Examples of inorganic compounds and vitamins as growth-aiding factors for microorganisms, derived from animals and plants include the following.

| Inorganic compounds | Vitamins |
| --- | --- |
| Potassium dihydrogen phosphate | Biotin |
| Magnesium sulfate | Folic acid |
| Manganese sulfate | Pyridoxine |
| Sodium chloride | Thiamine |
| Cobalt chloride | Riboflavin |
| Calcium chloride | Nicotinic acid |
| Zinc sulfate | Pantothenic acid |
| Copper sulfate | Vitamin B12 |
| Alum | Thioctic acid |
| Sodium molybdate | p-Aminobenzoic acid |
| Potassium chloride | |
| Boric acid and the like | |
| Nickel chloride | |
| Sodium tungstate | |
| Sodium selenate | |
| Ammonium ferrous sulfate | |
| Sodium acetate trihydrate | |
| Magnesium sulfate heptahydrate | |
| Manganese sulfate tetrahydrate | |

The growth can be improved in some cases by adding a reducing agent such as cysteine, cystine, sodium sulfate, sulfite, ascorbic acid, glutathione, thioglycolic acid, or rutin; or an enzyme that decomposes active oxygen species, such as catalase or superoxide dismutase, to the medium.

The gas phase and the aqueous phase during the culture preferably do not contain air or oxygen. For example, nitrogen and/or hydrogen is/are contained at an arbitrary ratio(s), or nitrogen and/or carbon dioxide is/are contained at an arbitrary ratio(s). The gas phase and the aqueous phase preferably contain hydrogen. From the viewpoint of promoting the production of the second urolithin, the ratio of hydrogen in the gas phase is usually not less than 0.5%, preferably not less than 1.0%, more preferably not less than 2.0%. On the other hand, the ratio is usually not more than 100%, preferably not more than 20%, more preferably not more than 10%.

The method for achieving such an environment of the gas phase and the aqueous phase during the culture is not limited. The method may be, for example, a method in which the gas phase is replaced with the above gas before the culture, a method in which, also during the culture, the above gas is further supplied from the bottom of the culture vessel, and/or supplied to the gas phase in the culture vessel, or a method in which the aqueous phase is bubbled with the above gas before the culture. As the hydrogen, hydrogen gas may be used as it is. Alternatively, a material(s) of hydrogen such as formic acid and/or a salt thereof may be added to the medium to allow production of hydrogen by an action of the microorganism during the culture.

The aeration rate is, for example, 0.005 to 2 vvm. An aeration rate of 0.05 to 0.5 vvm is preferred. The gas to be mixed may also be supplied as nanobubbles.

The culture temperature is preferably 20° C. to 45° C., more preferably 25° C. to 40° C., still more preferably 30° C. to 37° C.

The pressure condition of the culture vessel is not limited as long as the condition allows the growth. The pressure condition is, for example, within the range of 0.001 to 1 MPa, preferably 0.01 to 0.5 MPa.

The culture period is, for example, usually 8 to 340 hours, preferably 12 to 170 hours, more preferably 16 to 120 hours.

Production of the second urolithin can be promoted in some cases by addition of a surfactant, adsorbent, inclusion compound, or the like to the culture liquid.

Examples of the surfactant include Tween 80, which may be added at about 0.001 g/L to 10 g/L.

Examples of the adsorbent include cellulose and derivatives thereof; dextrin; the Diaion HP series and the Sepabeads series, which are hydrophobic adsorbents manufactured by Mitsubishi Chemical Corporation; and the Amberlite XAD series, manufactured by Organo Corporation.

Examples of the inclusion compound include α-cyclodextrin, β-cyclodextrin, γ-cyclodextrin, and cluster dextrin (highly branched cyclic dextrin). Among these, γ-cyclodextrin is most effective in some cases. By allowing coexistence of two or more kinds of inclusion compounds, the production of the second urolithin can be further promoted in some cases.

The total amount of the inclusion compound(s) to be added in terms of the molar ratio to the first urolithin is usually not less than 0.1 equivalents, preferably not less than 0.5 equivalents, more preferably not less than 1.0 equivalent. On the other hand, the total amount is usually not more than 5.0 equivalents, preferably not more than 2.5 equivalents, more preferably not more than 2.0 equivalents.

(Production of Second Urolithin by Resting Cells)

In cases where the microorganism having the ability to produce the second urolithin from the first urolithin is resting cells, the solution is preferably a salt solution or a buffer described in the "Resting Cells of Microorganism Having Ability to Produce Second Urolithin from First Urolithin" section, rather than the medium. Regarding other conditions, the descriptions in the "Medium, and Production of Second Urolithin by Culture" section are applied.

(First Urolithin)

The first urolithin in the first invention of the present invention may be prepared by any method. For example, the first urolithin may be synthesized by a chemical synthesis method or a fermentation method. In cases where the second urolithin produced by the first invention of the present invention is used as a food or drink, the first urolithin to be used therefor is preferably prepared by a fermentation method or an enzyme method using a food or drink or a material of a food or drink as a raw material.

Examples of the chemical synthesis method include a method described in Non-patent Document 1.

Examples of the fermentation method include a method in which a microorganism having an ability to produce the first urolithin from a raw material of the first urolithin is allowed, in a solution containing the raw material of the first urolithin, to produce the first urolithin from the raw material of the first urolithin.

(Steps that May be Included Before Step (a))

After the production of the first urolithin by the fermentation method, the first urolithin may be separated and/or purified for application to Step (a) as the first urolithin of Step (a). Alternatively, without performing the separation and/or the purification, the solution containing the first urolithin may be applied, as it is or after dilution or concentration, to Step (a) as the first urolithin of Step (a).

That is, the first invention of the present invention may include, before the Step (a), the following Steps (pre-a1) and (pre-a2) in this order, or may include the following Steps (pre-a1) and (pre-a3) in this order, as steps to be carried out in a system that is separate from the system in which the Step (a) is carried out.

Step (pre-a1): allowing, in a solution containing a raw material of the first urolithin, a microorganism having an ability to produce the first urolithin from the raw material of the first urolithin to produce the first urolithin from the raw material of the first urolithin.

Step (pre-a2): separating and/or purifying the first urolithin produced in Step (pre-a1), and applying the separated and/or purified first urolithin to Step (a) as the first urolithin of Step (a).

Step (pre-a3): applying the solution containing the first urolithin produced in Step (pre-a1), as it is or after dilution or concentration, to Step (a) as the first urolithin of Step (a).

(2) Step (b)

In the method for producing a urolithin as the first invention of the present invention, the following Step (b) is preferably included in addition to the Step (a), and the Step (a) and the Step (b) are preferably carried out in the same system.

Step (b): allowing, in a solution containing a raw material of the first urolithin, a microorganism having an ability to produce the first urolithin from the raw material of the first urolithin to produce the first urolithin from the raw material of the first urolithin.

(Same System)

The term "Step (a) and Step (b) are carried out in the same system" means that the series of processes from the production of the first urolithin in Step (b) from the raw material of the first urolithin by the microorganism having the ability to produce the first urolithin from the raw material of the first urolithin in the solution containing the raw material of the first urolithin, to the production of the second urolithin in Step (a) by the use of the resulting first urolithin as it is as the first urolithin of Step (a), is carried out continuously in the same system. That is, the term means that, for example, a step of separating and/or purifying the first urolithin produced in Step (b) is not included between Step (b) and Step (a).

More specifically, for example, the microorganism having the ability to produce the first urolithin from the raw material of the first urolithin and the microorganism having the ability to produce the second urolithin from the first urolithin are inoculated to the same culture liquid, and then cultured to produce the second urolithin. These microorganisms may be either the same kind of microorganism or different kinds of microorganisms.

In cases where the first urolithin is urolithin C, the Step (b) is read as Step (b1).

(Raw Material of First Urolithin)

The raw material of the first urolithin may be prepared by any method. This also applies to a raw material of the raw material of the first urolithin, a raw material of the former raw material, and further raw materials.

For example, such raw materials may be synthesized by a chemical synthesis method or a fermentation method. In cases where the second urolithin produced by the first invention of the present invention is used as a food or drink, the raw material of the first urolithin to be used therefor is preferably obtained by a fermentation method or an enzyme method.

Examples of the chemical synthesis method include a method described in Non-patent Document 1.

Examples of the fermentation method include a method in which the microorganism having the ability to produce the raw material of the first urolithin from a raw material of the raw material of the first urolithin is allowed, in a solution containing the raw material of the raw material of the first urolithin, to produce the raw material of the first urolithin from the raw material of the raw material of the first urolithin.

(Other Steps)

The first invention of the present invention may include the following steps.

The first invention of the present invention may include, for example, a step of quantifying the second urolithin obtained. The quantification method may be carried out according to a conventional method. For example, ethyl acetate to which an acid such as formic acid is added as required is added to the culture liquid, and the resulting mixture is then vigorously stirred, followed by centrifugation and then removal of the ethyl acetate layer. The same operation is carried out several times as required, and the resulting ethyl acetate layers are combined together to obtain a urolithin extract. The extract is then concentrated and dried under reduced pressure using an evaporator or the like, and dissolved in methanol. The resulting solution is filtered through a membrane such as a polytetrafluoroethylene (PTFE) membrane to remove insoluble matters, and then subjected to quantification by high-performance liquid chromatography. Examples of the conditions for the high-performance liquid chromatography include, but are not limited to, the following.

[Conditions for the High-Performance Liquid Chromatography]

Column: Inertsil ODS-3 (250×4.6 mm) (manufactured by GL Science)
Eluent: water/acetonitrile/acetic acid=74/25/1
Flow rate: 1.0 mL/min
Column temperature: 40° C.
Detection: 305 nm The first invention of the present invention may include a step of purifying, or a step of concentrating, the second urolithin obtained by the above step. As the purification treatment in the purification step, a treatment such as sterilization of the microorganism by heat or the like; elimination of the microorganism by microfiltration (MF), ultrafiltration (UF), or the like; removal of solid matters and macromolecular substances; extraction with an organic solvent or an ionic liquid; or adsorption or decoloration using a hydrophobic adsorbent, ion-exchange resin, activated carbon column, or the like; may be carried out. Examples of the concentration treatment in the concentration step include concentration using an evaporator, reverse osmosis membrane, or the like.

The solution containing the second urolithin may be pulverized by freeze-drying, spray drying, or the like. In the pulverization, an excipient such as lactose, dextrin, or corn starch may be added.

1-1. One Preferred Embodiment

One preferred embodiment of the present invention is described below.

The present embodiment is a mode in which the first urolithin is urolithin C; the second urolithin is urolithin A; and the microorganism having the ability to produce the second urolithin from the first urolithin is a microorganism belonging to the genus *Clostridium*.

That is, the present embodiment is a method for producing urolithin A, including the following Step (a1).

Step (a1): allowing, in a solution containing urolithin C, a microorganism belonging to the genus *Clostridium* having an ability to produce urolithin A from urolithin C to produce urolithin A from urolithin C.

(Medium, and Production of Urolithin a by Culture)

Examples of the inclusion compound in the present embodiment include α-cyclodextrin, β-cyclodextrin, γ-cyclodextrin, and cluster dextrin (highly branched cyclic dextrin). γ-Cyclodextrin is most effective, and α-cyclodextrin and β-cyclodextrin are also effective. By allowing coexistence of two or more kinds of inclusion compounds, the production of urolithin A can be further promoted in some cases.

(Raw Material of Urolithin C)

Examples of the raw material of the urolithin C include ellagic acid; ellagitannins such as punicalagin and geraniin, which are precursors of the ellagic acid; and urolithin M5, and urolithin D and urolithin M6, which are precursors of urolithin C. The raw material of urolithin C is preferably ellagic acid and/or ellagitannin.

The plant from which the ellagic acid and/or the ellagitannin is/are produced is not limited, and examples of the plant include pomegranate, raspberry, blackberry, cloudberry, boysenberry, strawberry, walnut, and geranium herb. Among these, pomegranate, boysenberry, and geranium herb are preferred since these contain large amounts of ellagic acid and/or ellagitannin. Pomegranate is more preferred.

The raw material of urolithin C is not limited as long as the microorganism having the ability to produce urolithin C from the raw material of urolithin C can be allowed to produce urolithin C from the raw material of urolithin C in a solution containing the raw material of urolithin C. One or more raw materials may be used.

(Microorganism Having Ability to Produce Urolithin C)

In the present embodiment, the microorganism having the ability to produce urolithin C from the raw material of urolithin C is not limited. For example, microorganisms belonging to the genus *Gordonibacter* and microorganisms belonging to the genus *Eggerthella* are preferred.

Among the microorganisms belonging to the genus *Gordonibacter*, microorganisms belonging to *Gordonibacter pamelaeae* and microorganisms belonging to *Gordonibacter urolithinfaciens* are more preferred.

Among the microorganisms belonging to *Gordonibacter pamelaeae*, the DSM 19378 strain is still more preferred. Among the microorganisms belonging to *Gordonibacter urolithinfaciens*, the DSM 27213 strain is still more preferred.

Among the microorganisms belonging to the genus *Eggerthella*, microorganisms belonging to *Eggerthella* sp. are preferred. The DC 3563 (NITE BP-02376) strain is more preferred.

One or more of the above microorganisms may be used irrespective of the genus, the species, and the strain of each microorganism.

The DC 3563 (NITE BP-02376) strain has been deposited to NITE Patent Microorganisms Depositary, National Institute of Technology and Evaluation [address: #122, 2-5-8 Kazusakamatari, Kisarazu-shi, Chiba 292-0818, Japan] as of Nov. 11, 2016 as international deposition in accordance with the Budapest Treaty.

(Resting Cells of Microorganism Having Ability to Produce Urolithin C)

The microorganism having the ability to produce urolithin C includes resting cells thereof. Regarding the resting cells, the descriptions in "Resting Cells of Microorganism Having Ability to Produce Second Urolithin from First Urolithin" are applied.

(Solution Containing Raw Material of Urolithin C)

The solution containing the raw material of urolithin C is not limited as long as the microorganism having the ability to produce urolithin C from the raw material of urolithin C can be allowed to produce urolithin C from the raw material of urolithin C in the solution. The solution is preferably a medium, more preferably a medium in the above-described "Medium, and Production of Second Urolithin by Culture" section. In cases where the microorganism is resting cells, the above-described salt solution or buffer is preferred.

The content of the raw material of urolithin C in the solution is usually not less than 0.01 g/L, preferably not less than 0.1 g/L, more preferably not less than 1.0 g/L. On the other hand, the content is usually not more than 100 g/L, preferably not more than 20 g/L, more preferably not more than 10 g/L.

(Medium, and Production of Urolithin C by Culture)

In cases where the microorganism having the ability to produce urolithin C from the raw material of urolithin C is allowed to produce urolithin C from the raw material of urolithin C in the solution containing the raw material of urolithin C, the solution is preferably a medium. Regarding details of more preferred media, culture conditions, and the like, the descriptions in the "Medium, and Production of Second Urolithin by Culture" section are applied.

Similarly to the cases described above, the production of urolithin C can be promoted in some cases by addition of a surfactant, adsorbent, inclusion compound, or the like to the culture liquid. Examples of the inclusion compound include α-cyclodextrin, β-cyclodextrin, γ-cyclodextrin, and cluster dextrin (highly branched cyclic dextrin). γ-Cyclodextrin is most effective, and α-cyclodextrin and β-cyclodextrin are also effective. By allowing coexistence of two or more kinds of inclusion compounds, the production of urolithin C can be further promoted in some cases.

The total amount of the inclusion compound(s) to be added in terms of the molar ratio to the total amount of the raw material of urolithin C is usually not less than 0.2 equivalents, preferably not less than 1.0 equivalent, more preferably not less than 2.0 equivalents. On the other hand, the total amount of the inclusion compound(s) is usually not more than 10.0 equivalents, preferably not more than 5.0 equivalents, more preferably not more than 4.0 equivalents.

(Production of Urolithin C by Resting Cells)

In cases where the microorganism having the ability to produce urolithin C from the raw material of urolithin C is resting cells, the solution is preferably a salt solution or a buffer described in the "Resting Cells of Microorganism Having Ability to Produce Second Urolithin from First Urolithin" section, rather than a medium. Regarding other conditions, the descriptions in the "Medium, and Production of Second Urolithin by Culture" section are applied.

1-2. One Preferred Embodiment

Another preferred embodiment of the present invention is described below.

The present embodiment is a mode in which the first urolithin is urolithin M5; the second urolithin is urolithin E; and the microorganism having the ability to produce the second urolithin from the first urolithin is a microorganism belonging to the genus *Clostridium*.

That is, the present embodiment is a method for producing urolithin E, including the following Step (a2).

Step (a2): allowing, in a solution containing urolithin M5, a microorganism belonging to the genus *Clostridium* having an ability to produce urolithin E from urolithin M5 to produce urolithin E from urolithin M5.

The urolithin M5 may be prepared by any method. As an example, the above-described mode for urolithin C in the method for producing urolithin A, including Step (a1) is applied.

Examples of the raw material of the urolithin M5 include ellagic acid; and ellagitannins such as punicalagin and geraniin, which are precursors of the ellagic acid. The raw material of the urolithin M5 is preferably ellagic acid and/or ellagitannin.

1-3. One Preferred Embodiment

Another preferred embodiment of the present invention is described below.

The present embodiment is a mode in which the first urolithin is urolithin M6; the second urolithin is urolithin M7; and the microorganism having the ability to produce the second urolithin from the first urolithin is a microorganism belonging to the genus *Clostridium*.

That is, the present embodiment is a method for producing urolithin M7, including the following Step (a3).

Step (a3): allowing, in a solution containing urolithin M6, a microorganism belonging to the genus *Clostridium* having an ability to produce urolithin M7 from urolithin M6 to produce urolithin M7 from urolithin M6.

The urolithin M6 may be prepared by any method. As an example, the above-described mode for urolithin C in the method for producing urolithin A, including Step (a1) is applied.

Examples of the raw material of the urolithin M6 include ellagic acid; ellagitannins such as punicalagin and geraniin, which are precursors of the ellagic acid; and urolithin M5, which is a precursor of urolithin M6.

1-4. One Preferred Embodiment

Another preferred embodiment of the present invention is described below.

The present embodiment is a mode in which the first urolithin is isourolithin A; the second urolithin is urolithin B; and the microorganism having the ability to produce the second urolithin from the first urolithin is a microorganism belonging to the genus *Clostridium*.

That is, the present embodiment is a method for producing urolithin B, including the following Step (a4).

Step (a4): allowing, in a solution containing isourolithin A, a microorganism belonging to the genus *Clostridium* having an ability to produce urolithin B from isourolithin A to produce urolithin B from isourolithin A.

The isourolithin A may be prepared by any method.

Examples of the raw material of the isourolithin A include ellagic acid; ellagitannins such as punicalagin and geraniin, which are precursors of the ellagic acid; and urolithin M5 and urolithin M6, as well as urolithin C, which is a precursor of isourolithin A.

For example, in cases where urolithin C is used as the raw material of isourolithin A, isourolithin A obtained by a method for producing isourolithin A, including a step of allowing a microorganism having an ability to produce isourolithin A from urolithin C to produce isourolithin A from urolithin C in a solution containing urolithin C may be used.

The microorganism having an ability to produce isourolithin A from urolithin C is not limited as long as it is a microorganism having an ability to produce isourolithin A from urolithin C. The microorganism is preferably an anaerobic microorganism.

Specific examples of the microorganism include microorganisms belonging to the genus *Slackia*. More specific examples of the microorganism include microorganisms belonging to *Slackia heliotrinireducens*. Still more specific examples of the microorganism include the *Slackia heliotrinireducens* DSM 20476 strain.

One or more of the above microorganisms may be used irrespective of the genus, the species, and the strain of each microorganism.

In cases where urolithin M5 is used as the raw material of isourolithin A, the above-described mode for urolithin M5 in the method for producing urolithin E, including Step (a2) is applied.

In cases where urolithin M6 is used as the raw material of isourolithin A, the above-described mode for urolithin M6 in the method for producing urolithin M7, including Step (a3) is applied.

Regarding other conditions, the above-described mode for urolithin C in the method for producing urolithin A, including Step (a1) is applied.

<2. Method for Producing Food or Drink Containing Second Urolithin>

The method for producing a food or drink containing the second urolithin as the second invention of the present invention includes the above Step (a) and the following Step (c), and may also include other steps. The food or drink to be produced by the second invention of the present invention includes supplements. The supplements are classified into a group of food or drink composed of dietary supplements.

(1) Step (a)

Regarding Step (a), the above descriptions for the Step (a) in the first invention of the present invention are applied.

(2) Step (c)

Step (c) is a step of mixing the second urolithin produced in the Step (a) with a raw material of a food or drink to provide the food or drink. The food or drink is produced according to a conventional method by mixing an ordinary raw material of the food or drink with the second urolithin produced in the Step (a), and the timing of the mixing is not limited. Examples of the raw material of the food or drink include food additives. Further, if necessary, the resulting food or drink may be enclosed in an appropriate container such as a bottle, bag, can, box, or pack.

The food or drink produced by the second invention of the present invention may contain, as a major component, water, protein, carbohydrate, lipid, vitamin, mineral, organic acid, organic base, juice, flavor, or the like.

Examples of the protein include animal and plant proteins such as whole milk powder, skimmed milk powder, semi-skimmed milk powder, casein, soy protein, chicken egg protein, and meat protein; hydrolysates thereof, and butter.

Examples of the carbohydrate include sugars, processed starches (dextrin, soluble starch, British starch, oxidized starch, starch ester, starch ether, and the like), and dietary fibers.

Examples of the lipid include lard; and vegetable oils and fats such as safflower oil, corn oil, rapeseed oil, and palm oil, and fractionated oils, hydrogenated oils, and transesterified oils thereof.

Examples of the vitamin include vitamin A, carotenes, vitamin Bs, vitamin C, vitamin Ds, vitamin E, vitamin Ks, vitamin P, vitamin Q, niacin, nicotinic acid, pantothenic acid, biotin, inositol, choline, and folic acid.

Examples of the mineral include calcium, potassium, magnesium, sodium, copper, iron, manganese, zinc, selenium, and whey minerals.

Examples of the organic acid include malic acid, citric acid, lactic acid, and tartaric acid.

Two or more of these components may be used in combination. These components may be synthetic products.

The content of the second urolithin produced in the Step (a) with respect to the total amount of the food or drink produced by the second invention of the present invention is not limited. The content is preferably a content with which an effect of the second urolithin such as antioxidant action, anti-inflammatory action, anti-saccharification action, mitophagy-promoting action, or the like can be obtained by ingestion of the food or drink.

The content of the second urolithin with respect to the total amount of the food or drink is usually not less than 0.0001% by mass, preferably not less than 0.001% by mass, more preferably not less than 0.01% by mass. The content is usually not more than 10% by mass, preferably not more than 1% by mass, more preferably not more than 0.1% by mass.

In cases where the food or drink is a supplement, it may be in any form such as a solid matter, gel-like product, or liquid product. Examples of the form include various processed foods and drinks, powders, tablets, balls, capsules, jellies, and granules. Further, if necessary, the supplement may be enclosed in an appropriate container such as a bottle, bag, can, box, or pack.

The supplement may contain an additive, and examples of the additive include excipients such as dextrin; preservatives such as vitamin C; corrigents such as vanillin; dyes such as safflower dye; monosaccharides, oligosaccharides, and polysaccharides (for example, glucose, fructose, sucrose, saccharose, and carbohydrates containing these); acidulants; perfumes; fats and oils; emulsifiers; whole milk powder; and agar. Two or more of these components may be used in combination. These components may be synthetic products.

EXAMPLES

The present invention is described below in more detail by way of specific examples. However, the present invention is not limited to these examples.

A urolithin having a hydroxyl group at the 9-position of the urolithin skeleton (Table 2) was added as a substrate to ABB medium (manufactured by Oxoid Limited), and then heat-sterilized, followed by replacing the gas phase with the $N_2:CO_2:H_2$ (80%/10%/10%) gas to provide a basal medium. To the basal medium containing each substrate at a final concentration of 1.0 g/L, the *Clostridium bolteae* JCM 12243 strain was inoculated, and culture was carried out anaerobically at 37° C. for 2 weeks. After completion of the culture, the same amount of ethyl acetate was added to 5 mL of the culture liquid to extract urolithin, and the resulting ethyl acetate phase was concentrated under reduced pressure, followed by drying. The thus obtained dried product was redissolved in 0.5 mL of methanol, and quantitative analysis of urolithin was carried out by HPLC.

The HPLC was carried out under the following conditions. Urolithins manufactured by DALTON PHARMA, after dissolution in DMSO, were used as standard samples.

The results are shown in Table 2. From the urolithins having a hydroxyl group at the 9-position, urolithins from which the hydroxyl group at the 9-position was eliminated were produced.

<HPLC Analysis Conditions>
Column: Inertsil ODS-3 (250×4.6 mm) (manufactured by GL Science)
Eluent: water/acetonitrile/acetic acid=74/25/1
Flow rate: 1.0 mL/min
Column temperature: 40° C.
Detection: 305 nm

TABLE 2

| Microorganism | Substrate | Concentration (g/L) | Product | Molar yield (%) |
|---|---|---|---|---|
| *Clostridium bolteae* JCM 12243 strain | Urolithin M5 | 1.0 | Urolithin E | 61.1 |
| | Urolithin M6 | 1.0 | Urolithin M7 | 98.7 |
| | Urolithin C | 1.0 | Urolithin A | 100 |
| | Isourolithin A | 1.0 | Urolithin B | 5.0 |

Example 2

Urolithin C as a precursor of urolithin A was added to ABB medium (manufactured by Oxoid Limited), and then heat-sterilized, followed by replacing the gas phase with the $N_2:CO_2:H_2$ (80%/10%/10%) gas to provide a basal medium. To the basal medium containing urolithin C at a final concentration of 1.0 g/L, the *Clostridium bolteae* DSM 15670 strain or DSM 29485 strain was inoculated, and culture was carried out anaerobically at 37° C. After completion of the culture, the same amount of ethyl acetate was added to 5 mL of the culture liquid to extract urolithin, and the resulting ethyl acetate phase was concentrated under reduced pressure, followed by drying. The thus obtained dried product was redissolved in 0.5 mL of methanol, and quantitative analysis of urolithin was carried out by HPLC.

The HPLC was carried out under the same conditions as in Example 1. Urolithins manufactured by DALTON PHARMA, after dissolution in DMSO, were used as standard samples. As a result, by 2 weeks of the culture, 100% or 89%, respectively, of the urolithin C added was converted to urolithin A.

Example 3

The same operation as in Example 2 was carried out except that the culture was carried out for 5 days using the *Clostridium asparagiforme* DSM 15981 strain. As a result, 95% of the urolithin C added was converted to urolithin A.

Example 4

The same operation as in Example 2 was carried out except that the culture was carried out for 5 days using the *Clostridium citroniae* DSM 19261 strain. As a result, 82% of the urolithin C added was converted to urolithin A.

Example 5

The *Clostridium bolteae* JCM 12243 strain and the *Gordonibacter pamelaeae* DSM 19378 strain were inoculated to ABB medium (manufactured by Oxoid Limited) supplemented with 0.1% ellagic acid (manufactured by SIGMA), and culture was carried out in the same manner as in Example 2. As a result of 2 weeks of the culture, 67% of the ellagic acid added was converted to urolithin A.

Example 6

Culture was carried out in the same manner as in Example 5 except that the *Clostridium bolteae* JCM 12243 strain and the *Gordonibacter urolithinfaciens* DSM 27213 strain were used. As a result of 2 weeks of the culture, 62% of the ellagic acid added was converted to urolithin A.

Example 7

Culture was carried out in the same manner as in Example 5 except that the *Clostridium asparagiforme* DSM 15981 strain and the *Gordonibacter urolithinfaciens* DSM 27213 strain were used. As a result of 5 days of the culture, 60% of the ellagic acid added was converted to urolithin A.

Example 8

Culture was carried out in the same manner as in Example 5 except that the *Clostridium citroniae* DSM 19261 strain and the *Gordonibacter urolithinfaciens* DSM 27213 strain were used. As a result of 5 days of the culture, 60% of the ellagic acid added was converted to urolithin A.

Example 9

Culture was carried out in the same manner as in Example 2 except that the amount of the urolithin C added was 0.81 g/L, and that the gas phase was nitrogen alone or nitrogen: hydrogen (90%/10%), in order to compare the influence of hydrogen on the production of urolithin A. The amount of urolithin A produced by 3 days of the culture with respect to the urolithin C added was 73% in the case where hydrogen was absent, and 86% in the case where hydrogen was present in the gas phase. Thus, the presence of hydrogen in the gas phase promoted the production of urolithin A.

Example 10

Culture was carried out in the same manner as in Example 2 except that the amount of urolithin C added was 0.81 g/L, and that 1.2 equivalents, in terms of the molar ratio to urolithin C, of α-cyclodextrin, β-cyclodextrin, or γ-cyclodextrin was added or not added, in order to compare the influence of each cyclodextrin on the production of urolithin A.

While the yield after 5 days of the culture was 47% in the case where no cyclodextrin was added, the yield was 78% in the case where α-cyclodextrin was added, 66% in the case where β-cyclodextrin was added, and 98% in the case where γ-cyclodextrin was added. Thus, the addition of cyclodextrin to the reaction liquid promoted the production of urolithin A.

INDUSTRIAL APPLICABILITY

According to the present invention, another kind of urolithin can be produced from a urolithin having a hydroxyl group at the 9-position, by elimination of the hydroxyl group at the 9-position.

The urolithin produced may be utilized for cosmetics, quasi drugs, medical products, sanitary articles, drugs, foods and drinks (including supplements), and the like that are to be used for antioxidation, anti-inflammation, anti-saccharification, and/or the like.

All prior art documents cited in the present description are herein incorporated by reference.

The invention claimed is:

1. A method for producing a second urolithin represented by the following General Formula (2), comprising the following Step (a):

Step (a): allowing, in a solution containing a first urolithin represented by the following General Formula (1), a microorganism having an ability to produce the second urolithin represented by the following General Formula (2) from the first urolithin to produce the second urolithin from the first urolithin

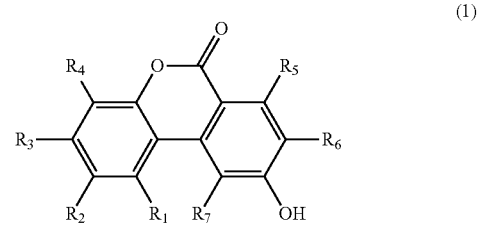

(1)

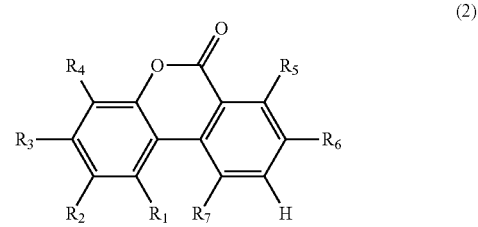

(2)

wherein $R_1$ to $R_7$ each represent a hydroxyl group, a hydrogen atom, or a methoxy group, and at least one of $R_1$ to $R_7$ represents a hydroxy group wherein $R_1$ to $R_7$ are identical to the $R_1$ to $R_7$, respectively, of the first urolithin represented by the General Formula (1), wherein the only microorganism in said solution having an ability to produce the second urolithin from the first urolithin is a microorganism belonging to the genus *Clostridium*.

2. The production method according to claim 1,
wherein the combination of the first urolithin and the second urolithin is a combination of urolithin M5 and urolithin E, respectively, a combination of urolithin M6 and urolithin M7, respectively, a combination of urolithin C and urolithin A, respectively, or a combination of isourolithin A and urolithin B, respectively.

3. The production method according to claim 1,
wherein the microorganism belonging to the genus *Clostridium* is at least one selected from the group consisting of a microorganism belonging to *Clostridium bolteae*, a microorganism belonging to *Clostridium asparagiforme*, and a microorganism belonging to *Clostridium citroniae*.

4. The production method according to claim 3,
wherein the microorganism belonging to *Clostridium bolteae* is at least one selected from the group consisting of the *Clostridium bolteae* JCM 12243 strain, DSM 15670 strain, and DSM 29485 strain.

5. The production method according to claim 3,
wherein the microorganism belonging to *Clostridium asparagiforme* is the *Clostridium asparagiforme* DSM 15981 strain.

6. The production method according to claim 3,
wherein the microorganism belonging to *Clostridium citroniae* is the *Clostridium citroniae* DSM 19261 strain.

7. The production method according to claim 2,
wherein the combination of the first urolithin and the second urolithin is a combination of urolithin C and urolithin A, respectively.

8. The production method according to claim 7,
wherein the urolithin C is obtained by allowing, in a solution containing a raw material of urolithin C, a microorganism having an ability to produce urolithin C from the raw material of urolithin C that is different from said *Clostridium* having an ability to produce the second urolithin from the first urolithin to produce urolithin C from the raw material of urolithin C.

9. The production method according to claim 7, further comprising the following Step (b1):
Step (b1): allowing, in a solution containing a raw material of urolithin C, a microorganism having an ability to produce urolithin C from the raw material of urolithin C that is different from said *Clostridium* having an ability to produce the second urolithin from the first urolithin to produce urolithin C from the raw material of urolithin C;
wherein the Step (a) and the Step (b1) are carried out in the same system.

10. The production method according to claim 8,
wherein the microorganism having an ability to produce urolithin C from the raw material of urolithin C is a microorganism belonging to the genus *Gordonibacter*.

11. The production method according to claim 10,
wherein the microorganism belonging to the genus *Gordonibacter* is a microorganism belonging to *Gordonibacter pamelaeae* and/or a microorganism belonging to *Gordonibacter urolithinfaciens*.

12. The production method according to claim 11,
wherein the microorganism belonging to *Gordonibacter pamelaeae* is the *Gordonibacter pamelaeae* DSM 19378 strain.

13. The production method according to claim 11,
wherein the microorganism belonging to *Gordonibacter urolithinfaciens* is the *Gordonibacter urolithinfaciens* DSM 27213 strain.

14. The production method according to claim 8,
wherein the raw material of urolithin C is ellagic acid and/or ellagitannin.

15. The production method according to claim 1,
wherein the Step (a) is carried out in an environment with a gas phase containing hydrogen.

16. The production method according to claim 15,
wherein the ratio of the hydrogen in the gas phase is not less than 0.5% and not more than 20%.

17. The production method according to claim 7,
wherein, in the Step (a), the solution containing urolithin C further contains at least one selected from the group consisting of inclusion compounds of α-cyclodextrin, β-cyclodextrin, and γ-cyclodextrin.

18. The production method according to claim 9,
wherein, in the Step (b1), the solution containing the raw material of urolithin C further contains at least one selected from the group consisting of inclusion compounds of α-cyclodextrin, β-cyclodextrin, and γ-cyclodextrin.

* * * * *